United States Patent
Grenon et al.

(10) Patent No.: US 7,981,095 B2
(45) Date of Patent: **\*Jul. 19, 2011**

(54) METHODS FOR TREATING MEIBOMIAN GLAND DYSFUNCTION EMPLOYING FLUID JET

(75) Inventors: Stephen M. Grenon, Hillsborough, NC (US); Lyle Paul, Russell, KY (US); Steven Roe, San Mateo, CA (US); Donald R. Korb, Boston, MA (US)

(73) Assignee: TearScience, Inc., Morrisville, NC (US)

( * ) Notice: Subject to any disclaimer, the term of this patent is extended or adjusted under 35 U.S.C. 154(b) by 699 days.

This patent is subject to a terminal disclaimer.

(21) Appl. No.: 11/541,291

(22) Filed: Sep. 29, 2006

(65) Prior Publication Data
US 2007/0049913 A1    Mar. 1, 2007

Related U.S. Application Data

(63) Continuation-in-part of application No. 11/434,033, filed on May 15, 2006.

(60) Provisional application No. 60/700,233, filed on Jul. 18, 2005.

(51) Int. Cl.
*A61M 35/00* (2006.01)
*A61F 7/00* (2006.01)
*A61B 18/04* (2006.01)

(52) U.S. Cl. ........ 604/294; 604/290; 604/289; 604/291; 607/104; 606/27

(58) Field of Classification Search .................. 604/289, 604/290, 291
See application file for complete search history.

(56) References Cited

U.S. PATENT DOCUMENTS
1,006,945 A    10/1911    Houston
(Continued)

FOREIGN PATENT DOCUMENTS
CA    2679448 A1    9/2008
(Continued)

OTHER PUBLICATIONS
Minco "Introducing: Thermofoil Heaters" Bulletin HS-202, 9 pages.
(Continued)

*Primary Examiner* — Leslie R Deak
*Assistant Examiner* — Susan Su
(74) *Attorney, Agent, or Firm* — Withrow & Terranova, PLLC

(57) ABSTRACT

According to the present invention, there is provided a method of treating meibomian gland dysfunction in a mammal wherein an occlusion blocks at least a portion of the flow of naturally occurring secretion out of a gland channel orifice. The invention comprises selecting a device capable of delivering a jet of heated medium. The device is positioned such that when the jet is it is applied to the exterior surface of the eyelid, proximate to the gland channel orifice, a jet of heated medium is applied to the exterior surface of the eyelid proximate to the gland channel orifice at a pressure of from about 2 psi to about 30 psi. Application of the jet of heated medium is maintained for sufficient time to loosen, break up, fracture, soften or liquefy at least a portion of the occlusion such that at least a portion of the occlusion is removed. In an exemplary embodiment, the medium is water heated to a temperature of between about 42° C. and about 46° C. Depending on the particular type and composition of the obstruction, the fluid jet operates to melt or soften the obstruction and to milkingly move the corpus of the softened obstruction up the gland channel from the end opposite the meibomian gland orifice and out of the gland orifice. Repeated application of the heated fluid jet may also be necessary to soften and/or express the obstruction.

27 Claims, 6 Drawing Sheets

U.S. PATENT DOCUMENTS

| | | | |
|---|---|---|---|
| 1,924,315 | A | 8/1933 | Hemphill et al. |
| 2,891,252 | A | 6/1959 | Lazo |
| 3,333,586 | A | 8/1967 | Bellis et al. |
| 3,404,678 | A | 10/1968 | Von Ardenne |
| 3,667,476 | A | 6/1972 | Muller |
| 4,261,364 | A | 4/1981 | Hadaddad et al. |
| 4,778,457 | A | 10/1988 | York |
| 4,883,454 | A | 11/1989 | Hamburg |
| 4,914,088 | A * | 4/1990 | Glonek et al. ............... 514/76 |
| 4,955,377 | A | 9/1990 | Lennox et al. |
| 4,958,632 | A | 9/1990 | Duggan |
| 5,030,214 | A | 7/1991 | Spector |
| 5,151,100 | A | 9/1992 | Abele et al. |
| 5,158,082 | A | 10/1992 | Jones |
| 5,213,097 | A | 5/1993 | Zeindler |
| 5,251,627 | A | 10/1993 | Morris |
| 5,283,063 | A | 2/1994 | Freeman |
| 5,343,561 | A | 9/1994 | Adamo |
| D352,106 | S | 11/1994 | Fanney et al. |
| 5,368,582 | A * | 11/1994 | Bertera ..................... 604/295 |
| 5,368,591 | A | 11/1994 | Lennox et al. |
| 5,425,380 | A | 6/1995 | Hudson et al. |
| 5,496,311 | A | 3/1996 | Abele et al. |
| 5,601,548 | A | 2/1997 | Smith et al. |
| 5,643,336 | A | 7/1997 | Lopez-Claros |
| 5,700,238 | A | 12/1997 | Hyson |
| 5,720,773 | A | 2/1998 | Lopez-Claros |
| 5,807,357 | A | 9/1998 | Kang |
| 5,836,927 | A | 11/1998 | Fried |
| 5,958,912 | A | 9/1999 | Sullivan |
| 5,964,723 | A | 10/1999 | Augustine |
| 6,024,095 | A | 2/2000 | Stanley, III |
| 6,107,289 | A | 8/2000 | Sullivan |
| 6,110,292 | A | 8/2000 | Jewett et al. |
| 6,112,900 | A | 9/2000 | Adkins, Jr. |
| 6,113,561 | A | 9/2000 | Augustine |
| 6,153,607 | A | 11/2000 | Pflugfelder et al. |
| 6,155,995 | A | 12/2000 | Lin |
| 6,181,970 | B1 | 1/2001 | Kasevich |
| 6,193,740 | B1 | 2/2001 | Rodriguez |
| 6,206,842 | B1 | 3/2001 | Tu et al. |
| 6,213,966 | B1 | 4/2001 | Augustine |
| 6,273,886 | B1 | 8/2001 | Edwards et al. |
| D456,079 | S | 4/2002 | Fujii |
| 6,423,018 | B1 | 7/2002 | Augustine |
| 6,425,888 | B1 * | 7/2002 | Embleton et al. ............. 604/290 |
| 6,438,398 | B1 | 8/2002 | Pflugfelder et al. |
| 6,455,583 | B1 | 9/2002 | Pflugfelder et al. |
| 6,482,203 | B2 | 11/2002 | Paddock et al. |
| 6,490,488 | B1 | 12/2002 | Rudie et al. |
| D472,637 | S | 4/2003 | Cooper et al. |
| 6,544,257 | B2 | 4/2003 | Karino et al. |
| D477,084 | S | 7/2003 | Menezes et al. |
| 6,641,264 | B1 | 11/2003 | Schwebel |
| 6,788,977 | B2 | 9/2004 | Fenn et al. |
| 6,827,898 | B1 | 12/2004 | Fausset et al. |
| 6,840,954 | B2 | 1/2005 | Dietz et al. |
| 6,860,852 | B2 | 3/2005 | Schonenberger et al. |
| 6,860,880 | B2 | 3/2005 | Treat et al. |
| 6,874,884 | B2 * | 4/2005 | Schwebel ..................... 351/62 |
| 6,882,885 | B2 | 4/2005 | Levy, Jr. et al. |
| 6,886,933 | B2 | 5/2005 | Schwebel |
| 6,908,195 | B2 * | 6/2005 | Fuller ........................ 351/158 |
| 6,925,317 | B1 | 8/2005 | Samuels et al. |
| 6,974,454 | B2 | 12/2005 | Hooven |
| 7,001,379 | B2 | 2/2006 | Behl et al. |
| 7,004,942 | B2 | 2/2006 | Laird et al. |
| 7,036,928 | B2 | 5/2006 | Schwebel |
| 7,069,084 | B2 | 6/2006 | Yee |
| 7,108,694 | B2 | 9/2006 | Miura et al. |
| 7,118,591 | B2 | 10/2006 | Frank et al. |
| 7,123,968 | B1 | 10/2006 | Casscells, III et al. |
| 7,211,070 | B2 * | 5/2007 | Soroudi ...................... 604/294 |
| 7,231,922 | B2 | 6/2007 | Davison et al. |
| D546,459 | S | 7/2007 | Banryu |
| D552,736 | S | 10/2007 | Yamaoka |
| D553,750 | S | 10/2007 | Yamaoka |
| 7,357,500 | B2 | 4/2008 | Schwebel |
| 7,442,174 | B2 | 10/2008 | Butler |
| 7,513,893 | B2 | 4/2009 | Soroudi |
| 7,594,728 | B2 | 9/2009 | Seal et al. |
| D612,941 | S | 3/2010 | Youngquist et al. |
| D614,774 | S | 4/2010 | Gausmann et al. |
| 7,712,899 | B2 | 5/2010 | Tanassi et al. |
| 2001/0041886 | A1 | 11/2001 | Durkin et al. |
| 2002/0035345 | A1 | 3/2002 | Beck |
| 2002/0099094 | A1 | 7/2002 | Anderson |
| 2002/0111608 | A1 | 8/2002 | Baerveldt et al. |
| 2002/0128696 | A1 | 9/2002 | Pearl et al. |
| 2003/0056281 | A1 | 3/2003 | Hasegawa |
| 2003/0065277 | A1 | 4/2003 | Covington |
| 2003/0114426 | A1 | 6/2003 | Pflugfelder et al. |
| 2003/0139790 | A1 | 7/2003 | Ingle et al. |
| 2003/0195438 | A1 | 10/2003 | Petillo |
| 2003/0211043 | A1 | 11/2003 | Korb |
| 2003/0233135 | A1 | 12/2003 | Yee |
| 2004/0064169 | A1 | 4/2004 | Briscoe et al. |
| 2004/0064171 | A1 | 4/2004 | Briscoe et al. |
| 2004/0076695 | A1 | 4/2004 | Gilbard |
| 2004/0111138 | A1 | 6/2004 | Bleam et al. |
| 2004/0153093 | A1 | 8/2004 | Donovan |
| 2004/0237969 | A1 | 12/2004 | Fuller |
| 2004/0249427 | A1 | 12/2004 | Nabilsi |
| 2005/0022823 | A1 | 2/2005 | Davison et al. |
| 2005/0119629 | A1 | 6/2005 | Soroudi |
| 2005/0143798 | A1 | 6/2005 | Bleam et al. |
| 2005/0220742 | A1 | 10/2005 | Breen |
| 2006/0018953 | A1 | 1/2006 | Gullion et al. |
| 2006/0030604 | A1 | 2/2006 | Elsinger et al. |
| 2006/0055878 | A1 | 3/2006 | Yee |
| 2006/0104914 | A1 | 5/2006 | Soroudi |
| 2006/0139569 | A1 | 6/2006 | Schwebel |
| 2006/0154901 | A1 | 7/2006 | Pflugfelder et al. |
| 2006/0157064 | A1 | 7/2006 | Davison et al. |
| 2006/0183698 | A1 | 8/2006 | Abelson |
| 2006/0233859 | A1 | 10/2006 | Whitcup et al. |
| 2007/0016256 | A1 | 1/2007 | Korb et al. |
| 2007/0049913 | A1 | 3/2007 | Grenon et al. |
| 2007/0173799 | A1 * | 7/2007 | Hsia ............................ 606/27 |
| 2007/0203462 | A1 | 8/2007 | Soroudi |
| 2007/0280924 | A1 | 12/2007 | Daniels et al. |
| 2008/0051741 | A1 | 2/2008 | Grenon et al. |
| 2008/0075787 | A1 | 3/2008 | Hibino |
| 2008/0132973 | A1 | 6/2008 | Lord et al. |
| 2009/0043365 | A1 | 2/2009 | Friedland et al. |
| 2009/0137533 | A1 | 5/2009 | Adkins, Jr. |
| 2009/0306111 | A1 | 12/2009 | Nakamura et al. |
| 2010/0100029 | A1 | 4/2010 | Maskin |
| 2010/0292630 | A1 | 11/2010 | Maskin |
| 2011/0039805 | A1 | 2/2011 | Pflugfelder et al. |
| 2011/0059902 | A1 | 3/2011 | Sullivan et al. |
| 2011/0059925 | A1 | 3/2011 | Donnenfeld |

FOREIGN PATENT DOCUMENTS

| | | |
|---|---|---|
| DE | 202005011496 U1 | 7/2006 |
| EP | 2151438 A1 | 2/2010 |
| EP | 1587468 B1 | 1/2011 |
| JP | 06269473 | 9/1994 |
| JP | 411221247 | 8/1999 |
| JP | 02002078727 | 3/2002 |
| JP | 2006 198249 | 8/2006 |
| JP | 201055012 A | 7/2010 |
| WO | PCT/US99/09965 | 11/1999 |
| WO | PCT/GB/2003/004782 | 5/2003 |
| WO | 2008024100 A2 | 2/2008 |
| WO | 2008106228 A2 | 9/2008 |
| WO | 2009064834 A2 | 5/2009 |

OTHER PUBLICATIONS

Unknown, "Anatomy of the Eye and Orbit," p. 170.

Paugh, J.R. et al., "Meibomian Therapy in Problematic Contact Lens Wear," Entrez PubMed, Optom Vis Sci. Nov. 1990; 68(11): 803-6, 1 page.

Tobler, David et al., "Nanotech Silver Fights Microbes in Medical Devices," ND & DI, devicelink.com, 1 page.
Unknown, "IFU Manual for PNT Model 1000—Rev H," 24 pages.
"New Over-the-Counter Dry Eye Drop Now Available to Help Estimated 40 Percent of Americans Who Suffer from Occasional or Chronic Dry Eye" Business Wire News Release, Published Mar. 31, 2008.
Gupta, S. et al. "Docetaxel-induced Meibomian Duct Inflammation and Blockage Leading to Chalazion Formation" Prostate Cancer Prostatic Diseases, vol. 10, No. 4, 2007.
Aronowicz, J D et al. "Short Term Oral Minocycline Treatment of Meibomiantis" Br. J Opthalmol, vol. 90, No. 7, Jul. 2006.
Goto, E. et al, "Treatment of Non-Inflamed Obstructive Meibomian Gland Dysfunction by an Infrared Warm Compression Device" Br J Opthalmol, vol. 86, No. 12, Dec. 2002.
"arGentis Licenses Third Treatment for Dry Eye Syndrome" www.businesswire.com, May 12, 2008.
Meibomian Gland Dysfunction and Contact Lens Intolerance, Korb et al., Journal of the American Optometric Association, vol. 51, No. 3 Mar. 1980 p. 243-251.
Impact of Antiandrogen Treatment on the Fatty Acid Profile of Neutral Lipids in Human Meibomian Gland Secretions, Sullivan et al. Jnl. Clinical Endrocrinogy & Metabolism, vol. 85, No. 12, p. 4866-4873, 2000.
Tear Film Lipid Layer Thickness and Ocular Comfort After Meibomian Therapy via Latent Heat with a Novel Device in Normal Subjects, Mitra et al., Eye (2004) 1-4.
Increase in Tear Film Lipid Layer Thickness Following Treatment of Meibomian Gland Dysfunction, Korb & Greiner, Lacrimal Gland, Tear Film & Dry Eye Syndromes, Plenum Press, 1994 pp. 293-298.
Poster 349-B349 Efficacy of the Treatment by the Disposable Eyelid Warming Instrument for Meibomian Gland Dysfunction, Goto et al., Sunday Apr. 30.
Disposable Eyelid-Warming Device for Treatment of Meibomina Gland Dysfunction, Mori, et al., Japan Journal of Ophthalmology, vol. 47, p. 578-586 (2003).
Conservative Treatment of Meibomian Gland Dysfunction, Romero et al. Contact Lens Ass'n of Ophthalmology, p. 14-19, Eye & Contact Lens vol. 30, p. 14-19 (2004).
The Therapeutic Role of Lipids-Managing Ocular Surface Disease, Lemp & Foulks, Supplement to Refractive Eyecare of Ophthalmologists, vol. 9, No. 6, Jun. 2005.
Treatment of non-inflamed Obstructive Meiboman Gland Dysfunction by an Infrared Warm Compression Device; Goto, et al., Br. J. Ophthalmology 2002:86: 1403-1407.
Tear Evaoporation Dynamics in Normal Subjects and Subjects with Obstructive Meibomian Gland Dysfunction; Goto et al., Investigative Opthalmology & Visual Science, Feb. 2003, vol. 44, No. 2, p. 533-539.
Conservative Treatment of Meibomian Gland Dysfunction; Romero et al. Eye & Contact Lens30(1):14-19,2004.
Tear Function Changes of-Postmenopausal Women In Response to Hormone Replacement Therapy, Kuscu et al, Maturitas 44 (2003) 63-68.
Increase in Tear Film Lipid Layer Thickness Following Treatment with Warm Compresses in Patients with Meibomian Gland Dysfunction, Olson et al., Eye & Contact Lens 29(2): 96-99, 2003.
Blackie, Caroline A. et al., "Inner Eyelid Surface Temperature as a Function of Warm Compress Methodology," Optometry and Vision Science, vol. 85, No. 8, Aug. 2008, pp. 675-683.
Kokke, K.H. et al., "Oral Omega-6 Essential Fatty Acid Treatment in Contact Lens Associated Dry Eye," Contact Lens and Anterior Eye, vol. 31, No. 3, 2008, pp. 141-146.
Korb, Donald R., Slide entitled "Inner Eyelid Surface Temperature as a Function of Warm Compress Methodology," from presentation entitled "The Tear Film and Dry Eye States A Fertile Research Area," University of California at Berkeley, School of Optometry, Apr. 11, 2008. 2 pages.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.

Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Paugh, Jerry R. et al., "Precorneal Residence Time of Artificial Tears Measured in Dry Eye Subjects," Optometry and Vision Science, vol. 85, No. 8, Aug. 2008, pp. 725-731.
Lemp, Michael A. et al., "Blepharitis in the United States 2009: A Survey-Based Perspective on Prevalence and Treatment." Ocul. Surf, vol. 7, No. 2 Suppl, Apr. 2009, pp. S1-S14.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Toyos, Rolando, "Intense Pulsed Light for Dry Eye Syndrome," Cataract & Refractive Surgery Today, Apr. 2009, pp. 1-3.
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Suzuki, Tomo et al., "Estrogen and Progesterone Control of Gene Expression in the Mouse Meibomian Gland," Invest. Ophthalmol. Vis. Sci., vol. 49, No. 5, Apr. 2008, pp. 1797-1818.
Vasta, Stephanie, "Aggressive Treatments Developed for Meibomian Gland Dysfunction," Primary Care Optometry News, Nov. 1, 2009, 3 pages.
Blackie, Caroline A. et al., "Recovery Time of an Optimally Secreting Meibomian Gland," Cornea, vol. 28, No. 3, Apr. 2009, pp. 293-297.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. et al., "Tear Film Lipid Layer Thickness as a Function of Blinking," Cornea, vol. 13, No. 4, 1994, pp. 354-359.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Butovich, Igor et al., "Meibomian Lipid Glands and the Impact of Temperature," Investigative Opthalmology & Visual Science vol. 51, No. 11, Nov. 2010, pp. 5508-5518.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.
Wang, Y. et al., "Baseline Profiles of Ocular Surface and Tear Dynamics After Allogeneic Hematopoietic Stem Cell Transplantation in Patients With or Without Chronic Gvhd-Related Dry Eye," Bone Marrow Transplantation, vol. 45, No. 6, Jun. 2010, pp. 1077-1083.
Korb, Donald R. et al., "Lid Wiper Epitheliopathy and Dry Eye Symptoms," Eye & Contact Lens, vol. 31, No. 1, 2005, pp. 2-8.
Foulks, Gary N., "Meibomian Gland Dysfunction: The Past, Present, and Future," Eye and Contact Lens, vol. 36, No. 5. Sep. 2010, pp. 249-253.
Blackie, Caroline A . et al., "Nonobvious Obstructive Meibomian Gland Dysfunction" Cornea, vol. 29, No. 12, Dec. 2010, pp. 1333-1345.
Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.

Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).

Non-Final Rejection mailed Jun. 17, 2009, for U.S. Appl. No. 11/434,446.

Final Rejection mailed Dec. 23, 2009, for U.S. Appl. No. 11/434,446.

Advisory Action mailed Mar. 4, 2010, for U.S. Appl. No. 11/434,446.

Non-Final Rejection mailed Apr. 9, 2010, for U.S. Appl. No. 11/434,446.

Restriction/Election Requirement mailed Oct. 1, 2010, for U.S. Appl. No. 11/434,033.

Non-Final Rejection mailed Jan. 24, 2011, for U.S. Appl. No. 11/434,033.

Friedland, B., et al., "A novel thermodynamic treatment for meibomian gland dysfunction," Current Eye Research, vol. 36, No. 2, Feb. 2011, pp. 79-87.

* cited by examiner

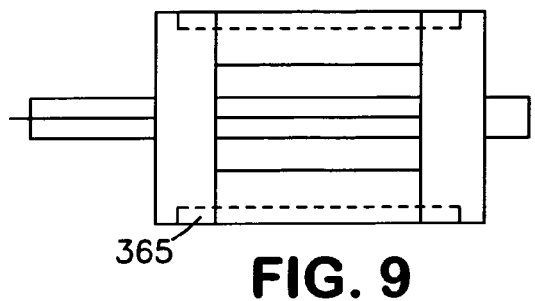
FIG. 9
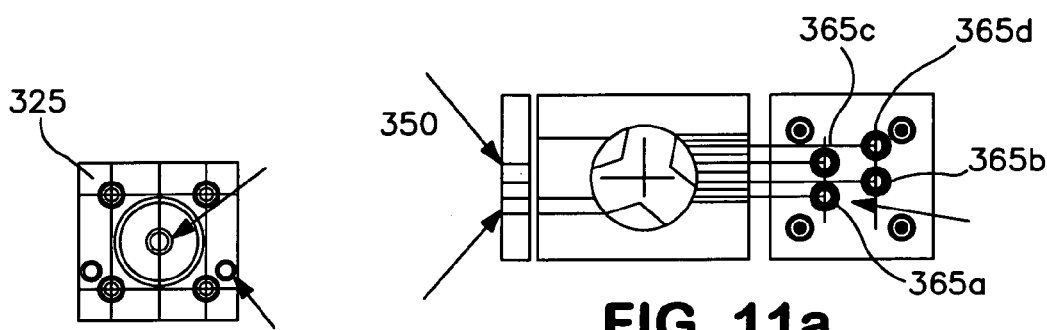
FIG. 10
FIG. 11a
FIG. 11b
FIG. 11c
FIG. 11d

_US 7,981,095 B2_

METHODS FOR TREATING MEIBOMIAN GLAND DYSFUNCTION EMPLOYING FLUID JET

CROSS REFERENCE TO RELATED DOCUMENTS

This application is a Continuation-In-Part of U.S. patent application Ser. No. 11/434,033 filed May 15, 2006 and entitled Method and Apparatus for Treating Meibomian Gland Dysfunction Employing Fluid Jet to Grenon et al., which claims priority benefit of U.S. Provisional Application 60/700,233, filed Jul. 18, 2005, both of which are hereby incorporated by reference.

This application is also related to U.S. patent application Ser. No. 11/434,054 entitled Method and Apparatus for Treating Meibomian Gland Dysfunction filed May, 15, 2006 to Korb, et al. and U.S. patent application Ser. No. 11/434,446 entitled Method and Apparatus for Treating Gland Dysfunction filed May 15, 2006 to Korb, et al., each of which is hereby incorporated by reference.

FIELD OF THE INVENTION

This invention relates generally to the field of treatment of the meibomian glands in humans to restore natural secretory function of lipids there from and to the tear film of the eye.

BACKGROUND OF THE INVENTION

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located on both the upper and lower eye lids, with orifices designed to discharge the lipid secretions onto the lid margins, thus forming the lipid layer of the tear film. The typical upper eyelid has about 25 meibomian glands and the lower eyelid has about 20 meibomian glands, which are somewhat larger than those located in the upper lid. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the lid margin at and around the junction of the inner mucous membrane and the outer skin of the eyelids termed the mucocutaneous junction.

Specifically, each meibomian gland has a straight long central duct lined with four epithelial layers on the inner surface of the duct. Along the length of the central duct there are multiple lateral out-pouching structures, termed acini, where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

Blinking causes the upper lid to pull a sheet of the lipids secreted by the meibomian glands upward over the other two layers of the tear film, thus forming a type of protective coating which limits the rate at which the underlying layers evaporate. Thus, it will be seen that a defective lipid layer or an incorrect quantity of such lipids can result in accelerated evaporation of the aqueous layer which, in turn, causes symptoms such as itchiness, burning, irritation, and dryness, which are collectively referred to as "dry eye".

Dry eye states have many etiologies. A common cause of common dry eye states is the condition known as "meibomian gland dysfunction" (MGD), a disorder where the glands are obstructed or occluded. A common cause of common dry eye states is a disorder where the glands are obstructed or occluded, usually referred to as "meibomian gland dysfunction" (MGD). As employed herein the terms "occluded" and "obstruction" as they relate to meibomian gland dysfunction are defined as partially or completely blocked or plugged meibomian glands, or any component thereof, having a solid, semi-solid or thickened congealed secretion and/or plug, leading to a compromise, or more specifically, a decrease or cessation of secretion. Also with a reduced or limited secretion the meibomian gland may be compromised by the occluded or obstructive condition as evidenced by a yellowish color indicating a possible infection state, or may be otherwise compromised so that the resulting protective lipid protective film is not adequate.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions are comprised of bacteria, sebaceous ground substance, dead, and/or desquamated epithelial cells, see, Korb et al., Meibomian Gland Dysfunction and Contact Lens Intolerance, Journal of the Optometric Association, Vol. 51, Number 3, (1980), pp. 243-251. While meibomitis is obvious by inspection of the external lids, mild to moderate and even severe obstructive meibomian gland dysfunction may not be obvious even when examined with the magnification of the slit-lamp biomicroscope, since there may not be external signs or the external signs may be so minimal that they are overlooked. The external signs of obstructive meibomian gland dysfunction may be limited to subtle alterations of the meibomian gland orifices, overgrowth of the epithelium of the lid margins over the orifices, and pouting of the orifices of the glands with congealed material acting as obstructions. The external signs of obstructive meibomian gland dysfunction in sever to very severe instances may be obvious, and include serration and distortion of the shape of the lid margins. While inflammation is not usually present with mild to moderate obstructive meibomian gland dysfunction, with severe to very severe instances of obstructive meibomian gland dysfunction, inflammation may be present.

Hormonal changes, which occur during menopause and particularly changing estrogen levels, can result in thickening of the oils secreted by the meibomian glands which results in clogged gland orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice thus further restricting sebum flow and exacerbating the dry eye condition. Additional factors which may cause or exacerbate meibomian gland dysfunction include, age, disorders of blinking, activities such as computer use which compromise normal blinking, contact lens wear and hygiene, cosmetic use or other illness.

The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained (see Korb, et al., "Increase in Tear Film Lipid Layer Thickness Following Treatment of Meibomian Gland Dysfunction", Lacrimal Gland, tear Film, ad Dry Eye Syndromes, pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye".

While the tear film operates as a singular entity and all of the layers thereof are important, the lipid layer, which is secreted from the meibomian glands, is of particular significance as it functions to slow the evaporation of the underlying layers and to lubricate the eyelid during blinking, both of which prevents dry eye and epitheliopathies.

Thus, to summarize, the meibomian glands of mammalian (e.g., human) eyelids secrete oils that prevent evaporation of the underlying tear film and provide lubrication to the eye These glands can become blocked or plugged by various mechanisms leading to excess evaporation of the tear film, compromised lubrication and so-called "dry eye syndrome". While not the only cause, meibomian gland dysfunction (MGD) is known to be a major cause of dry eye syndrome. The disorder is characterized by a blockage of some sort within the meibomian glands or at their surface preventing normal lipid secretions from flowing. Such secretions serve to lubricate the eye, hence their absence can cause dry eye syndrome. Obstructions or occlusions of the meibomian glands may be present over or at the orifice of the gland, in the main channel of the gland, or possibly in other locations including the passages from the acini to the main channel which may be narrowed or blocked. It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe® and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in United States Patent Publication no. US2003/011426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover) to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in Keratoconjuctivitis Sicca as disclosed in U.S. Pat. No. 5,958,912 and U.S. Pat. No. 6,107,289 both titled "Ocular Therapy in Keratoconjunctivitis Sicca Using Topically Applied Androgens or TGF-B" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely. However, no good method of applying localized heat to the eyelids and controlling the amount of heat applied is presently commercially available.

One modality for the heat treatment of meibomian gland dysfunction is disclosed in European Patent Application serial no. PCT/GB2003/004782 titled "Eyelid Margin Wipes Comprising Chemical Means for Temperature Adjustment". As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without drawbacks in that lid irritation can be exacerbated by non-specific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm² of energy operating on electrical power. Goto, E., et al. Treatment of Non-Inflamed Obstructive Meibomian Gland dysfunction by an Infrared Warm Compression Device, British Journal of Ophthalmology, Vol. 86 (2002), pp. 1403-1407. This device is designed as a non-contact infrared heating mask using IR light emitting diodes. However, there are many potential problems with use of an IR heating mechanism. For example, the IR Heat can penetrate beyond the eyelid into the Cornia which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat.

United States Patent Publication US2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects by Mitra et al, published in *Eye*, (2004) at pages 1-4.

United States Patent Publication US2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

Manual expression of the gland can be painful and is invasive with inconsistent results due to variations in manual control and/or manipulation. This method of treating MGD is also quite uncomfortable to the patient because it requires the physician to squeeze the glands. In addition, there are about 40 to 50 glands between the upper and lower lid, therefore, it is very time consuming to squeeze each gland. This is inefficient for the physician and Uncomfortable for the patient to endure.

It is therefore an object of the present invention to provide a meibomian gland treatment that overcomes the drawbacks and deficiencies of the prior art.

Another object of the present invention is to provide a meibomian gland treatment that is a single step treatment, thus, eliminating the need for manual expression.

Yet another object of the present invention is to provide a meibomian gland treatment which treats meibomian gland disease and not merely its symptoms.

Still another object of the present invention is to provide a-meibomian gland treatment that restores the natural sebum flow out of the meibomian glands rather than merely attempting to replace or replicate the naturally occurring tear components.

A still further object of the present invention is to provide a meibomian gland treatment which minimizes the chance of infection.

A still further object of the present invention is to provide a meibomian gland treatment that is simple, inexpensive, and easy to use by the health care provider and the patient.

SUMMARY OF THE INVENTION

According to the present invention, there is provided a method of treating meibomian gland dysfunction in a mammal wherein an occlusion blocks at least a portion of the flow of naturally occurring secretion out of a gland channel orifice. The invention comprises selecting a device capable of delivering a jet of heated medium. The device is positioned such that when the jet is it is applied to the exterior surface of the eyelid, proximate to the gland channel orifice, a jet of heated medium is applied to the exterior surface of the eyelid proximate to the gland channel orifice at a pressure of from about 2 psi to about 30 psi. Application of the jet of heated medium is maintained for sufficient time to loosen, break up, fracture, soften or liquefy at least a portion of the occlusion such that at least a portion of the occlusion is removed.

BRIEF DESCRIPTION OF THE DRAWINGS

FIG. 9 is a front view of the rotor distributor valve according to the present invention.

FIG. 10 is a side view of the input and output ports of rotor distributor valve according to the present invention.

FIGS. 11*a* through 11*d* illustrate the path of fluid into the rotor distributor valve, through the rotor and the corresponding distributor exit port.

DETAILED DESCRIPTION OF THE PREFERRED EMBODIMENTS

While the present invention will be described more fully hereinafter, it is to be understood at the outset that persons of skill in the art may modify the invention herein described while still achieving the favorable results of this invention. Accordingly, the description that follows is to be understood as a broad teaching disclosure directed to persons of skill in the appropriate arts, and not as limiting upon the present invention.

Figure 1:
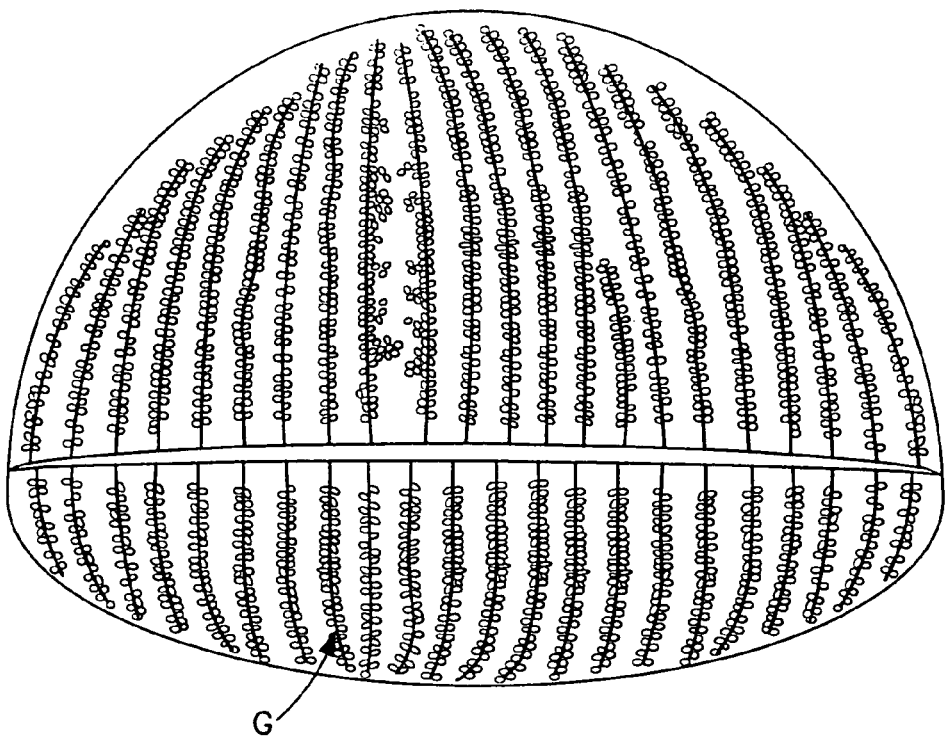
FIG. 1 is a schematic cut away view of the upper and lower eyelids illustrating the meibomian glands in cross section.
Figure 2:
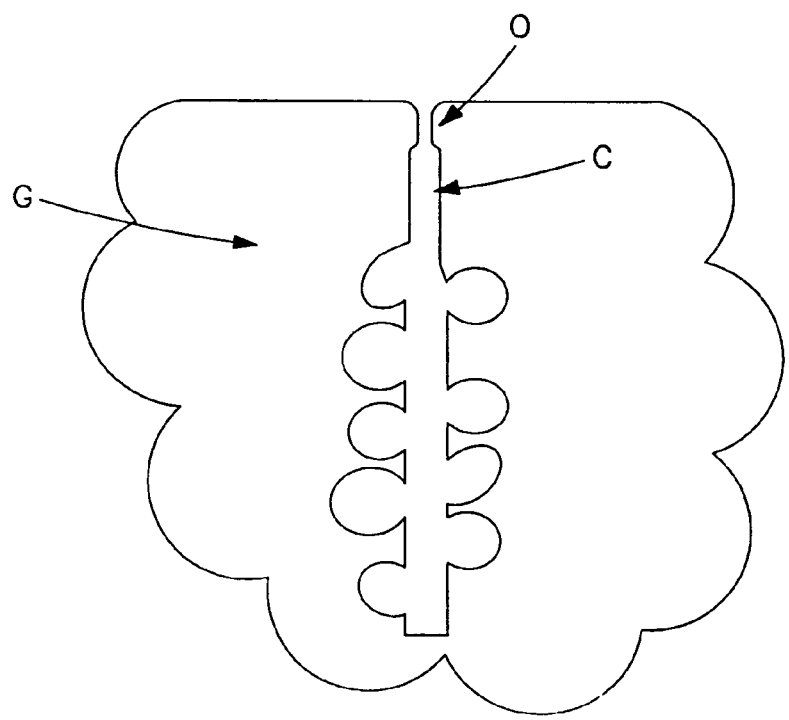
FIG. 2 is a cross sectional view of a single meibomian gland.

Referring now to FIG. 1, the location of the meibomian glands M are shown on the upper and lower eyelids. As briefly stated herein above, the upper lid contains approximately 25 meibomian glands and the lower lid contains approximately 20 meibomian glands. As shown in FIG. 2, each gland includes a channel C into which the secretion flows and an orifice O which opens on to the eyelid margin and through which the secretion must flow in order to be added to the tear film upon blinking. It will be seen that the glands are of different size, depending upon the location in the eyelid and that the orifice O is narrower than the channel C.

As briefly mentioned herein above, obstruction composition will vary with the etiology which produced it. However, the obstruction will, in most cases, consist of a combination of, dead cells, keratin, bacteria, desquamated cells, sebaceous ground substance, milky fluid, inspissated or creamy secretions; or any combination of the foregoing in solid, semi-solid and thickened forms. The obstruction may be in the gland channel, at the gland orifice, atop the gland orifice or a combination of the foregoing. As employed herein, obstruction refers to any of the foregoing.

Thus, it is self-evident that any obstruction of the channel will restrict or prevent secretions from exiting the gland and further, that in order to clear such obstructions or "occlusions", the obstruction may be loosened from the gland wall, and/or broken up, fractured, softened, or liquefied so that it will fit through the gland orifice without causing excessive pain. Lastly, the obstruction remnants must be expressed from the gland. The present invention provides a method and apparatus to accomplish these tasks.

According to the present invention, the obstruction P (or at least a portion thereof) should be loosened, broken up, softened or liquefied prior to attempting extraction or expression. With respect to the foregoing, the terms "loosened", "broken up" "softened" or "liquefied" are intended to mean a "non-solid" at least partially flowable state. In addition, in order to be clinically satisfactory, softening or liquefying of the obstruction P should be effected as quickly as possible and regulated heat treatment time should be as short as possible and the typical patient will require treatment for less than twenty (20) minutes, however, depending on the type and degree of obstruction, longer treatment periods or even multiple treatments may be necessary. It will be noted that the present treatment, even with longer treatment times does not cause damage to the surrounding tissues of the ocular globe or the eye. According to the present invention such heat treatment is provided by means of a heated fluid jet applied to the exterior surface of the eyelid. This necessarily requires the addition of a greater amount of energy (heating) than is deliverable by the conventional application of hot compresses which according to current practice are applied for 3-15 minutes prior to the clinician attempting to remove the obstruction. One of the problems with current techniques such at the use of hot compresses, is that the temperature of the heat source begins to drop almost immediately and the present inventors have learned, that in order to soften the obstruction, the temperature must be maintained between about 42° C. and about 46° C.

Once the occlusion is loosened, which may be defined as partially broken up, fractured, softened, or liquefied, in whole or in part such that at least a portion of the occlusion is removed from the walls of the gland, it may be operated upon such that it will pass through the orifice O in a manner which causes little or no pain or discomfort to the patent. This can be accomplished by heating to soften or liquefy the obstruction up to a range of thirty seven degrees centigrade (37° C.) to fifty degrees centigrade (50° C.) with the preferred operating range being forty degrees centigrade (40° C.) to forty eight degrees centigrade (48° C.) and desired modality of forty two degrees centigrade (42° C.) to forty six degrees centigrade (46° C.) so that it easily passes through the orifice (or with minimal non-painful expansion thereof.

Figure 3:
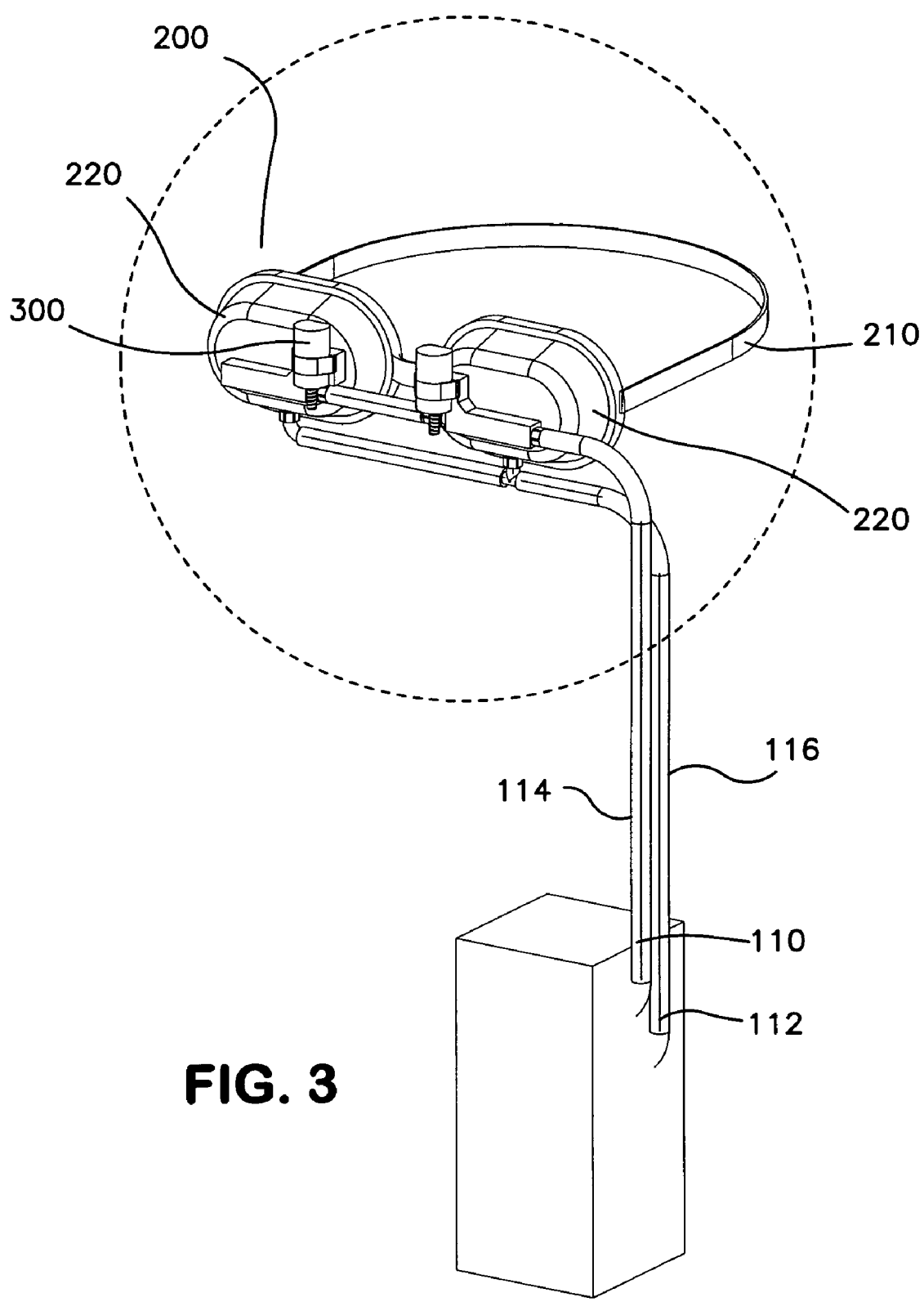
FIG. 3 is a perspective view of the proposed system for treating meibomian gland disease according to the present invention.
Figure 4:
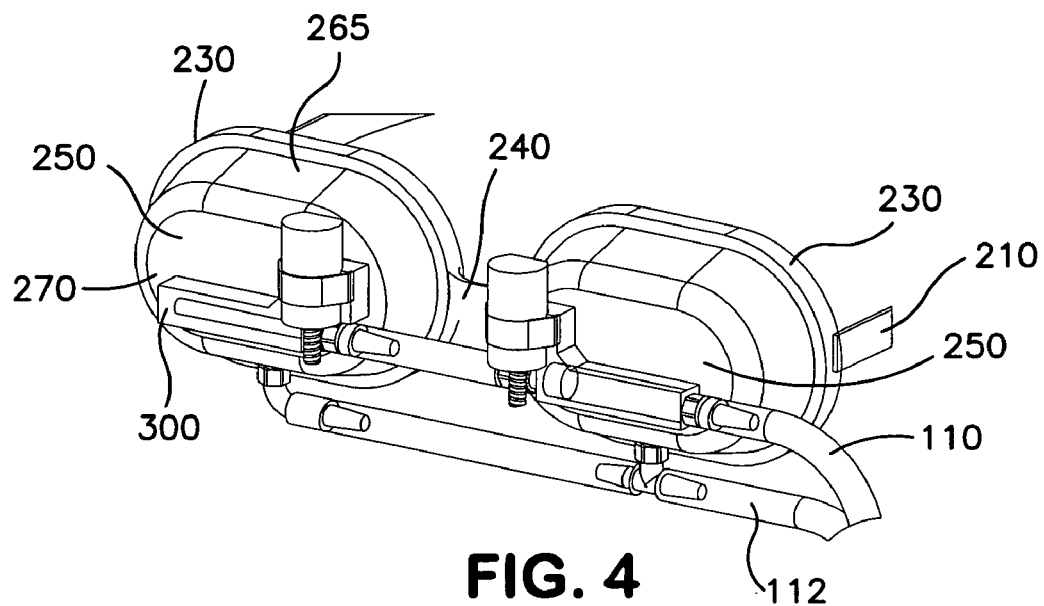
FIG. 4 is a front perspective view of the goggles according to the present invention.

While the present invention will be described with respect to the use of water as the preferred medium, the invention can be executed using a variety of other pumpable mediums such as gases (i.e., air), other liquids (glycerin, oils and the like) and creams. As illustrated in FIG. 3, the apparatus comprises a means for applying a jet of a heated fluid to the exterior surface of the eyelid proximate the occluded meibomian gland. The means comprises broadly a pump 100, goggles 200, and means for delivering a fluid jet to the meibomian glands G.

Further, the terms "proximate the gland" or "proximate to the gland" are meant herein that the fluid jet is directed to a position on the patient sufficiently close to the gland to be expressed or treated such that it will aid in pushing the obstruction from the gland. That position may vary from patient to patient being closer or further from the gland to be treated, but it is within the skill of the practitioner to find a position for each gland on each patient which will accomplish removal of the obstruction.

As illustrated in FIG. 3 the apparatus comprises a pump 100 which may be either AC (wall plug) or DC (battery) powered (not shown). The pump should be between 1/32 hp and 1/8 hp, with 1/16 hp being preferred based upon currently available data. One such pump is model STQP with pump head Q3CKC manufactured by Fluid Metering, Inc. of Syosset, N.Y. The pump 100 has respective fluid inlet and outlet ports 110,112. Attached to the respective inlet and outlet ports 110, 112 is a conduit such as Polyester® tubing 114,116 which connects to a goggle-type mask generally indicated at 200. Further, the pump 100 may be equipped with a heater (not shown) that heats the medium to the desired temperature. It will be noted that the preferred temperature of forty two degrees centigrade (42° C.) to forty six degrees centigrade (46° C.) is not the fluid temperature at the pump exit, but rather is the temperature of the fluid at the exit of the fluid delivery means 300. Thus, should the heater be located proximate the pump 100, the temperature may have to be higher in order to account for a temperature drop as the fluid travels to the goggles. Alternatively, the heater may be positioned on the tubing proximate the fluid inlet of goggles or mask 200 where the temperature drop would be minimal due to proximity to the meibomian gland and fast transit time through the apparatus to the meibomian gland. Depending upon the type of heated medium employed and the location of the heater itself, heat may be supplied by means of conduction, convection or radiation, as appropriate.

Mask 200 includes a headband 210 which is connected to the outer edges of mask eyepieces 220. Headband 210 should be fabricated from a flexible material such as rubber, but should maintain the eyepieces firmly in place against the orbit and cheek areas surrounding the eye. The respective eyepieces are substantially identical in structure and function and for ease of description reference will be made to "an eyepiece" or a component thereof. The eyepiece 220 comprises an oval annulus or ring 230 of a flexible material such as rubber, plastic or neoprene of a size sufficient to cover the orbit of the eye and the eyelids and to create a seal there around. The respective eyepieces are connected together with a nose piece or bridge 240, which in the preferred embodiment is integrally molded with the eyepieces. Similarly, the nose bridge 240 may be a separately attached component, such as in conventional swim goggles. One side of the ring 230 is adapted to lie flush with on the skin of the user and the opposite side is adapted to mount a lens 250 via conventional means (such as adhesive bonding or overmolding) to form a water tight seal. The techniques for lens mounting are well known to those skilled in the art. The lens 250 is integrally molded as a single clear unit and has a bottom wall 255, side walls 260, top wall 265 and front wall 270 which together define a cavity. Drain opening 275 is molded into the bottom wall 255 and front wall 270 has a slit opening 280 which mounts the means for delivering a jet of a heated medium or jet means 300 to the meibomian gland G to be described in greater detail herein below.

The jet means or rotary distributor valve 300 comprises a cylindrical manifold 305 having a bore (not shown) extending along its length. A spiral pattern of jet orifices 310 are positioned along a portion of the length of manifold 305 and each of respective orifices 310 is in fluid communication with the bore. The manifold 305 may also be equipped with a "neutral"

position in which no fluid is permitted to exit the orifices 310. At one end of manifold 305 is an integrally molded gear 315 and a nipple 320 at each end. The manifold 305 is mounted for rotation between the nipples. One nipple serves as the fluid inlet and the other serves as the fluid outlet. A housing 325 having a bore surrounds the manifold 305 which is snugly mounted for rotation therein. The housing 325 has a longitudinal slit 330 which allows fluid from the respective jet orifices 310 to pass there through such that upon rotation of the manifold, the jet orifices 310 are sequentially exposed to the slit 330 and fluid is directed at the eyelid. A small electric or water driven motor 340 is attached to the goggles such that the drive shaft thereof rotates gear 315.

Referring now to FIGS. 8 through 11a-d, another proposed embodiment of the rotary distributor valve 300 is illustrated in detail. The valve 300 comprises a housing 325 and a rotor or manifold 327 that has three vanes 355 and is mounted for rotation in the housing Positioned on the surface of housing 325 facing the eyelid are a plurality of ports or openings that are in fluid communication with the rotor. Fluid enters the valve 300 through feed port 350 and enters rotor vanes 355. As rotor 327 is rotated by the motor 340, the fluid passes through the vanes 355 and is aligned so that it exits through exhaust ports 365. Motor 340 may be a 324:1 reduction ratio DC motor such as Series 1512 available from FTB. Fluid leaking around the rotor 327 is expelled through the drain port 360. The operation of rotary distributor valve 300 is schematically illustrated in FIGS. 11a through 11d. FIG. 11a illustrates the vane 355 in alignment with port 365a with ports 365 c,d,e being closed. As vane 355 rotates (FIG. 11b), ports 365 a and b are open, with c and d remaining closed. Further rotation of vane 355 opens 365 a, b and c, with d remaining closed (FIG. 11c) and lastly, continued rotation closes port a, with ports b, c and d being open. The respective open ports are indicated by the arrows in FIGS. 11a-11d. Treatment would consist of multiple rotations of the vane and corresponding massage pressure from the respective jets. However, care should be taken to ensure that the jet pressure is less than that which would cause injury to the surface of the cornea should the jet accidentally contact the corneal surface.

Figure 5:
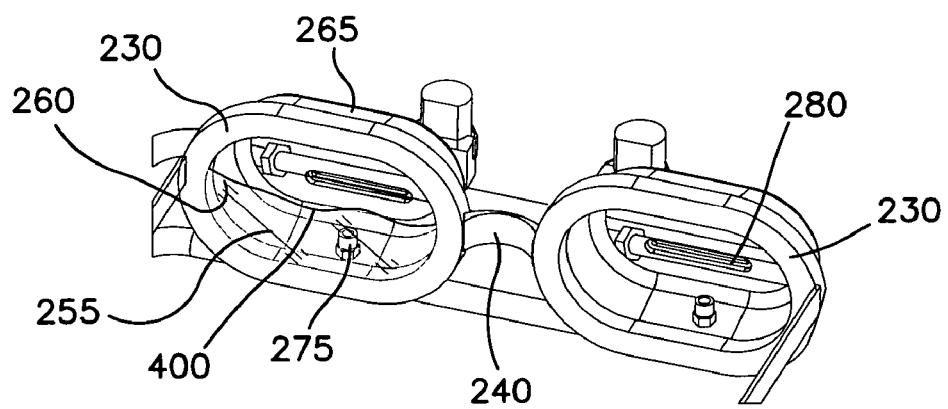
FIG. 5 is a rear perspective view of the goggles according to the present invention.
Figure 6:
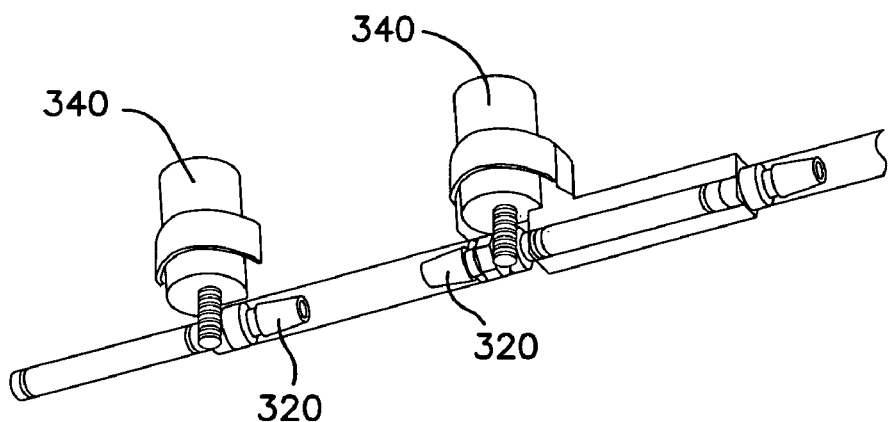
FIG. 6 is a front perspective view, taken from below and showing the fluid delivery components.
Figure 7:
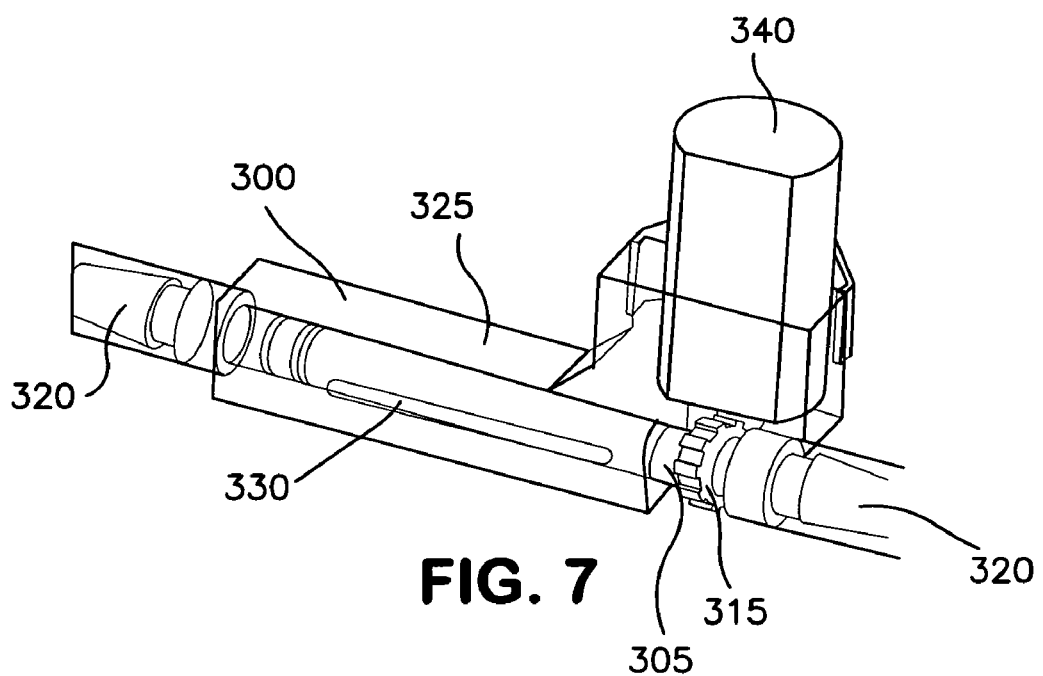
FIG. 7 is a rear perspective view fluid jet orifices according to the present invention.
Figure 8:
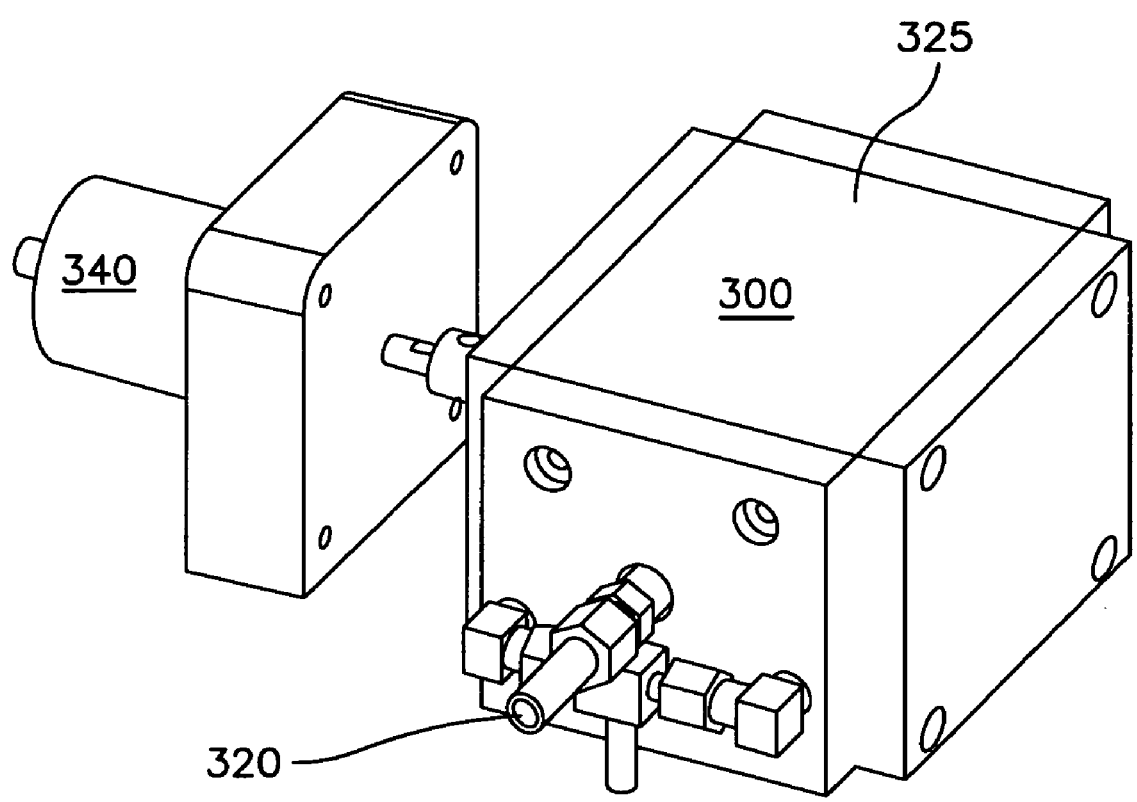
FIG. 8 illustrates the motor and fluid jet assembly for use on one eye according to the present invention.

In another aspect of the invention, a thin flexible membrane 400 (shown in one eyepiece in FIG. 5, such as a plastic membrane (not shown) can be located within the goggle cavity and positioned such that when in place on the eye of the patient, the membrane is substantially in contact with and covers the eyelid. The membrane operates to define a closed chamber into which the fluid jet is directed and which strikes the membrane. The force of the fluid jet is then transmitted through the intervening membrane and the eyelid into the meibomian gland in order to soften and express the obstruction.

In operation, the patient or healthcare provider would position the device, i.e., the goggles 200 over their eyes with the headband 210 extending around the head to hold the goggles in place such that when the jet of the heated medium is delivered, it is applied to the exterior surface of the eyelid, proximate the meibomian gland(s) to be treated. As previously mentioned, the goggles should be firmly, but comfortably in place to as not to move upon actuation of the apparatus. Alternatively, the device may be manually held in place against the head. Upon activation of the pump 100, the heated fluid begins to move through tubing 114, 116. During the initial start up period of the apparatus, the fluid is circulated by pump 100 and is heated to the required temperature. Once the preferred operating temperature has been reached, the motor 340 is activated and gear 315 begins to rotate, which in turn rotates manifold 305. As manifold 305 rotates, the jets line up sequentially with the slit and the fluid jet is directed on to the exterior surface of the eyelid proximate the occluded meibomian gland. Further, the fluid jet and the slit are constructed such that the fluid jet may be directed from the bottom of the meibomian gland upwards to the orifice end in order to impart a "milking" or upward "massage" type-motion to soften the obstruction and move it upward towards the gland orifice and out of the gland. Further, the fluid jet may also be pulsatory in nature wherein the fluid jet is intermittent. This intermittency may be effected for the jet operating upon a single gland from below upwards towards the orifice, pulsatory across multiple glands. Other pulsatory configurations are also possible. As the manifold 305 rotates, a continuous side to side scan of the eye lid with warm water jets and by allowing only one jet on each eye to be active at any instant in time, effective massage pressure is maximized, while discomfort is minimized. After the fluid has impacted the eyelid, it is collected in drain opening 275 and is drained out of the system loop. In another embodiment of the invention, the water jet may be applied to the surface of the eyelid in a "raster" type pattern wherein the meibomian gland is effectively scanned from side to side in lines from top to bottom to milkingly move the softened obstructive material along the meibomian gland from the end opposite the meibomian gland orifice toward the gland orifice. Thus, this raster pattern of scanning the eyelid or directing the jet to only one or a small area of the eyelid, results in a pulsatile type of force which reduces the patient's perceived pain level and thus, increases the overall pain threshold. It is believed that jet pulse frequencies of less than 300 Hz are effective. Depending upon the composition of the obstruction, repeated application of the heated fluid to the affected gland may be required. The jet of the heated medium should be maintained for sufficient time to loosen, break up, fracture, soften or liquefy at least a portion of the occlusion such that at least a portion of the occlusion is removed.

The invention may also employ a chemical agent to clean the gland margin and to remove or exfoliate cells from the meibomian gland orifice. For example Ophthaine® or a similar pharmacological agent may be employed to assist in removing epithelial cells from over the gland orifice. A probe similar to that shown in FIG. 5 may be employed, except that the inner tube will deliver the chemical agent and the suction applied by the outer covering will be used to evacuate the used chemical agent and cellular material mixture away from the gland margin. Similarly, the heating and vibrational features discussed above may also be employed.

Another embodiment of the invention employs the use of chemical or pharmacological agents to open or dilate the gland and gland orifice wherein the obstruction naturally is expressed and returns the normal secretions of the gland. Alternatively, the chemical or pharmaceutical agent would be used to soften or breakup the obstruction with such obstruction being expressed with the use of devices as defined above or combinations thereof. Chemical or pharmacological agents may also be used in connection with the device for post treatment. Once the glands have been opened then chemical or pharmacological agents may be used to enhance the normal production or secretion to maintain the glands in its unblocked state.

Dilation of the meibomian gland channel and orifice may also be employed to loosen or free the obstruction from the gland walls. Dilation may be accomplished by chemical, pharmacological, or mechanical means.

Stimulation of the meibomian gland may also be employed in conjunction with the other modalities discussed above to loosen or fracture the obstruction.

As mentioned herein above, the present invention has been described in detail on conjunction with the figures in connection with the meibomian glands of the eye. The reader will note that the principals of this invention may be applied with equal efficacy to the other glands of the human body and potentially to valuable domesticated farm animals to treat various ailments.

That which is claimed is:

1. A method of treating meibomian gland dysfunction in a mammal wherein an occlusion blocks at least a portion of the flow of naturally occurring secretion out of a gland channel orifice comprising:
   a) selecting a device capable of delivering a jet of heated medium;
   b) positioning the device such that when the jet is delivered it is applied to the exterior surface of a closed eyelid, proximate to the gland channel orifice;
   c) applying a jet of heated medium to the exterior surface of the closed eyelid proximate to the gland at a pressure of from about 2 psi to about 30 psi;
   d) maintaining application of the jet of heated medium to the closed eyelid for sufficient time to loosen, break up, fracture, soften or liquefy at least a portion of the occlusion such that at least a portion of the occlusion is removed.

2. A method according to claim 1 wherein the jet is applied in a pulsatory manner.

3. A method according to claim 1 wherein the jet is applied at a frequency between 1 Hz and 300 Hz.

4. A method according to claim 1 wherein the jet is applied at a frequency between 5 Hz and 60 Hz.

5. A method according to claim 1 wherein the heated medium is applied at a temperature of at least 42° C.

6. A method according to claim 1 wherein the device is positioned by attaching the device to the mammal.

7. A method according to claim 1 wherein the device is positioned by manually holding the device.

8. A method according to claim 1 wherein the jet may be repositioned during application of the jet.

9. A method according to claim 1 wherein the jet may not be repositioned during application of the jet.

10. A method according to claim 1 wherein the jet is applied to the exterior surface of the closed eyelid through an intervening membrane.

11. A method according to claim 1 wherein the jet is directly applied to the exterior surface of the closed eyelid.

12. A method of treating meibomian gland dysfunction in a mammal wherein an occlusion blocks at least a portion of the flow of naturally occurring secretion out of a gland channel orifice comprising:
   a) selecting a device capable of delivering a jet of heated medium;
   b) positioning the device such that when the jet is delivered it is applied to the exterior surface of a closed eyelid, proximate to the gland channel orifice;
   c) applying a jet of heated medium to the exterior surface of the closed eyelid proximate to the gland channel orifice at a pressure of from about 2 psi to about 30 psi;
   d) intermittently maintaining application of the jet of heated medium to the closed eyelid for sufficient time to loosen, break up, fracture, soften or liquefy at least a portion of the occlusion such that at least a portion of the occlusion is removed.

13. A method according to claim 12 wherein the jet is applied in a pulsatory manner.

14. A method according to claim 13 wherein the jet is applied at a frequency of between 1 Hz and 300 Hz.

15. A method according to claim 13 wherein the jet is applied at a frequency of between 5 Hz and 60 Hz.

16. A method according to claim 12 wherein the heated medium is applied at a temperature of at least 42° C.

17. A method according to claim 12 wherein the device is positioned by attaching the device to the mammal.

18. A method according to claim 12 wherein the device is positioned by manually holding the device.

19. A method according to claim 12 wherein the jet may be repositioned during application of the jet.

20. A method according to claim 12 wherein the jet may not be repositioned during application of the jet.

21. A method according to claim 12 wherein the jet is indirectly applied to the exterior surface of the closed eyelid through an intervening membrane.

22. A method according to claim 12 wherein the jet is directly applied to the exterior surface of the closed eyelid.

23. The method according to claim 12 wherein jet is heated by the modalities selected from the group consisting of conduction, convection and radiation.

24. The method according to claim 12 wherein the jet is applied to the meibomian gland in a manner that milkingly moves up the meibomian gland channel from the end opposite the meibomian gland orifice toward the gland orifice.

25. The method according to claim 12 wherein the jet is selected from the group consisting of fluid, gas, and flowable creams.

26. The method according to claim 12 further including the step of positioning a protective membrane over the eye and applying the jet of the heated medium to the membrane such that the jet pressure is transmitted there through and is absorbed by the closed eyelid.

27. The method according to claim 26 wherein the jet is pulsatory.

* * * * *